United States Patent
Sudol

(10) Patent No.: US 9,293,690 B2
(45) Date of Patent: Mar. 22, 2016

(54) ULTRASOUND TRANSDUCER ASSEMBLY AND METHOD OF MANUFACTURING THE SAME

(75) Inventor: Wojtek Sudol, Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 263 days.

(21) Appl. No.: 14/125,958

(22) PCT Filed: Jun. 26, 2012

(86) PCT No.: PCT/IB2012/053216
§ 371 (c)(1),
(2), (4) Date: Dec. 13, 2013

(87) PCT Pub. No.: WO2013/001448
PCT Pub. Date: Jan. 3, 2013

(65) Prior Publication Data
US 2014/0139072 A1  May 22, 2014

Related U.S. Application Data

(60) Provisional application No. 61/501,307, filed on Jun. 27, 2011.

(51) Int. Cl.
| H01L 41/08 | (2006.01) |
| A61B 8/00 | (2006.01) |
| H04R 17/00 | (2006.01) |
| H01L 41/29 | (2013.01) |
| B06B 1/06 | (2006.01) |
| H01L 41/047 | (2006.01) |

(52) U.S. Cl.
CPC .............. *H01L 41/29* (2013.01); *A61B 8/4494* (2013.01); *B06B 1/0607* (2013.01); *B06B 1/0622* (2013.01); *H01L 41/0475* (2013.01); *Y10T 29/42* (2015.01)

(58) Field of Classification Search
USPC .................. 310/322, 334; 29/25.35; 600/459
See application file for complete search history.

(56) References Cited

U.S. PATENT DOCUMENTS

| 5,774,960 | A | 7/1998 | De Fraguier et al. |
| 5,793,149 | A | 8/1998 | Thiel et al. |
| 6,726,631 | B2 | 4/2004 | Hatangadi et al. |
| 8,450,187 | B2 * | 5/2013 | Fukuyo et al. ................ 438/460 |
| 8,519,511 | B2 * | 8/2013 | Fujii et al. .................... 257/618 |
| 2008/0273424 | A1 | 11/2008 | Wodnicki et al. |
| 2008/0315331 | A1 | 12/2008 | Wodnicki et al. |
| 2010/0168583 | A1 | 7/2010 | Dausch et al. |

FOREIGN PATENT DOCUMENTS

EP  0785826 B1  2/1999

* cited by examiner

*Primary Examiner* — Thomas Dougherty

(57) ABSTRACT

The present invention relates to an ultrasound transducer assembly (100) comprising ultrasound transducer elements (175, 175a) for transmitting ultrasound waves in a general transmission direction (A). Each of or each of part of the ultrasound transducer elements (175, 175a) comprises a piezoelectric layer (110, 110a) having a top surface, a bottom surface and a side surface with respect to the general transmission direction (A), as well as a bottom electrode layer (111, 111a) and a top electrode layer (112, 112a). A conductive layer (125) is applied at least partly on the side surface of at least one specific one (110a) of the piezoelectric layers, such that the conductive layer (125) is connected to the top electrode layer (112a) and the bottom electrode layer (111a) of said specific piezoelectric layer (110a).

13 Claims, 6 Drawing Sheets

ULTRASOUND TRANSDUCER ASSEMBLY AND METHOD OF MANUFACTURING THE SAME

This application is the U.S. National Phase application under 35 U.S.C. §371 of International Application No. PCT/2012/053216, filed on Jun. 26, 2012, which claims the benefit of U.S. Provisional Patent Application No. 61/501,307, filed on Jun. 27, 2011. These applications are hereby incorporated by reference herein.

FIELD OF THE INVENTION

The present invention relates to an ultrasound transducer assembly comprising ultrasound transducer elements for transmitting ultrasound waves in a general transmission direction. The present invention further relates to a method of manufacturing such ultrasound transducer assembly.

BACKGROUND OF THE INVENTION

US 2008/0315331 A1 discloses a transducer assembly having a ground connection routed through a via formed in a cMUT array and through an ASIC. A transducer module comprises a cMUT transducer subarray formed on a semiconductor substrate with a front electrode positioned over a membrane and with the membrane suspended over insulating supports. The individual cells include bottom electrodes for receiving signals from ASIC circuit cells. A conductive via is formed within the insulating support between adjacent transducer cells to connect the front electrode to a contact on the cMUT substrate. However, the transducer assembly disclosed in US 2008/0315331 A1 is quite complex and thus not easy in manufacturing.

SUMMARY OF THE INVENTION

It is an object of the present invention to provide an ultrasound transducer assembly and corresponding method of manufacturing that provides an easier manufacturing and thus a cheaper ultrasound transducer assembly.

In a first aspect of the present invention an ultrasound transducer assembly is presented that comprises ultrasound transducer elements for transmitting ultrasound waves in a general transmission direction. Each of, or each of part of, the ultrasound transducer elements comprises a piezoelectric layer having a top surface, a bottom surface and a side surface with respect to the general transmission direction, as well as a bottom electrode layer and a top electrode layer. Further, a conductive layer is (directly) applied at least partly on the side surface of at least one specific one of the piezoelectric layers, such that the conductive layer is connected to the top electrode layer and the bottom electrode layer of said specific piezoelectric layer.

In a further aspect of the present invention a method of manufacturing an ultrasound transducer assembly is presented, the assembly comprising ultrasound transducer elements for transmitting ultrasound waves in a general transmission direction. The method comprises, for each of, or each of part of, the ultrasound transducer elements, providing a piezoelectric layer having a top surface, a bottom surface and a side surface with respect to the general transmission direction. The method further comprises, for each of, or each of part of, the ultrasound transducer elements, arranging or applying a bottom electrode layer, and arranging or applying a top electrode layer. The method further comprises (directly) applying a conductive layer at least partly on the side surface of at least one specific one of the piezoelectric layers, such that the conductive layer is connected to the top electrode layer and the bottom electrode layer of said specific piezoelectric layer.

In another aspect a method of manufacturing an ultrasound transducer assembly is presented, the assembly comprising ultrasound transducer elements for transmitting ultrasound waves in a general transmission direction. The method comprises providing a common layer of piezoelectric material having a top, surface, a bottom surface and a side surface. The method further comprises applying a common bottom electrode layer on the bottom surface of the common piezoelectric layer, applying a common top electrode layer on the top surface of the common piezoelectric layer, and applying a conductive layer on each of the side surfaces of the common piezoelectric layer, such that the conductive layer is connected to the common top electrode layer and the common bottom electrode layer. The method further comprises cutting or dicing the ultrasound transducer elements out of the coated common layer of piezoelectric material.

With general transmission direction a general direction is meant in which the ultrasound waves are transmitted from the ultrasound transducer element(s). In particular, the top surface or top electrode layer is arranged further in front in the general transmission direction than the bottom surface or bottom electrode layer. The general transmission direction can be in particular perpendicular to a surface formed by the tops of the ultrasound transducer elements. The bottom surface and the top surface of the piezoelectric layer can each be arranged perpendicular to the general transmission direction and/or the side surface can be arranged parallel to the general transmission direction. When a voltage is applied between the top electrode layer and the bottom electrode layer, ultrasound waves are transmitted from the piezoelectric layer in the general transmission direction. The bottom electrode layer acts as a bottom electrode for the piezoelectric layer or transducer element. The top electrode layer acts as a top electrode for the piezoelectric layer or transducer element.

Preferably, the bottom electrode layer is applied on the bottom surface of the piezoelectric layer, and the top electrode layer applied on the top surface of the piezoelectric layer. Alternatively, there can also be intermediate layers between the piezoelectric layer and the electrodes.

The basic idea of the invention is to provide a short electrical path between the top electrode(s) and an external electrical connection, in particular to ground. A conductive layer is (directly) applied at least partly, in particular on all of, the side surface of at least one specific one of the piezoelectric layers, such that the conductive layer is connected to the top electrode layer and the bottom electrode layer of said specific piezoelectric layer. With (directly) applying the conductive layer it is meant that there is or are no intermediate layer(s) between the piezoelectric layer and the applied conductive layer. The conductive layer provides electrical connection between the top electrode layer and the bottom electrode layer of said specific piezoelectric layer for external electrical connection, in particular for external electrical connection to ground. Alternatively, also external electrical connection to a voltage potential can be provided. By providing an electrical path from the top electrode layer to the bottom electrode layer of that specific piezoelectric layer, or corresponding ultrasound transducer element, a short electrical path, in particular for ground return current, is provided and at the same time the manufacturing process is easy.

Preferred embodiments of the invention are defined in the dependent claims. It shall be understood that the claimed method of manufacturing has similar and/or identical preferred embodiments as the claimed ultrasound transducer assembly and as defined in the dependent claims. In the same way it shall be understood that the claimed ultrasound transducer assembly has similar and/or identical preferred embodiments as the claimed method of manufacturing and as defined in the dependent claims.

In one embodiment the ultrasound transducer element having the specific piezoelectric layer is a dummy element not operable to transmit or receive ultrasound waves. By providing an electrical path between the top electrode layer and the bottom electrode layer of that specific piezoelectric layer or corresponding ultrasound transducer element, the piezoelectric layer is not functional any more. Thus, that specific ultrasound transducer element is a dummy element not operable to transmit or receive ultrasound waves. Therefore, that specific transducer element is sacrificed, as it is not functioning as a transducer element any more. However, even though that specific ultrasound transducer element is sacrificed, the manufacturing of the ultrasound transducer assembly is significantly simplified, thus providing a cheaper ultrasound transducer assembly.

In a further embodiment the ultrasound transducer element having the specific piezoelectric layer is the outermost ultrasound transducer element in a (one-dimensional) row or an (two-dimensional) array of the ultrasound transducer elements. In this way the conductive layer is applied to the outermost ultrasound transducer assembly, thus providing an easy way of applying the conductive layer. In a variant of this embodiment the side surface to which the conductive layer is applied is the side surface facing outward in the row or the array of the ultrasound transducer elements.

In a further variant of this embodiment, the ultrasound transducer elements having the specific piezoelectric layers are the outermost ultrasound transducer elements at the ends of a (one-dimensional) row or an (two-dimensional) array of ultrasound transducer elements. In this way, part of or all of the ultrasound transducer elements at the two ends of the (one-dimensional) row or the edges of the (two-dimensional) array of ultrasound transducer elements can be dummy elements not operable to transmit or receive ultrasound waves. With one-dimensional row an arrangement of transducer elements in only one direction is meant (arranged one next to the other in a row). With two-dimensional array an arrangement of the transducer elements in two directions is meant (arranged in rows and columns).

In a further embodiment the assembly further comprises a conductive connection layer which electrically connects the top electrode layers of the ultrasound transducer elements. This is an easy way of providing a common top electrode for external electrical connection, in particular to ground. In one example, the conductive connection layer can be (directly) applied to the top electrode layers or it can form the top electrode layers. In another example, there can be additional conductive layers between the top electrode layer and the conductive connection layer.

In a further embodiment, the assembly further comprises at least one matching layer applied to the top electrode layer and/or at least one de-matching layer applied to the bottom electrode layer. In this way, the performance of the ultrasound transducer assembly can be improved. By providing at least one matching layer, in particular multiple matching layers, to the top electrode impedance matching to the body of the user (patient), on which the ultrasound transducer assembly can be placed, is achieved. By providing at least one de-matching layer, in particular exactly one de-matching layer, to the bottom electrode reflection of basically all of the transmitted energy of the ultrasound waves in the general transmission direction can be achieved. The matching layer and/or de-matching layer can in particular be made of a conductive material. In one example, the matching layer(s) can be made of graphite and/or the de-matching layer(s) can be made of Tungsten or Tungsten carbide.

In a variant of this embodiment the conductive layer is further applied on the side surface of the at least one matching layer and/or de-matching layer. As it may be difficult to apply the conductive layer on only part of the specific ultrasound transducer element (stack of layers), applying the conductive layer also on the side surface of the matching layer(s) and/or de-matching layer(s) provides an easier way of manufacturing. The whole side surface of the stack of layers can thus be coated with one conductive layer.

In a variant of this variant a top conductive layer applied to the topmost matching layer and/or a bottom conductive layer applied to the bottommost de-matching layer. As it may be difficult to apply the conductive layer on only a side surface of the specific ultrasound transducer element, applying also a top conductive layer and/or a bottom conductive layer to the stack of layers provides an easier way of manufacturing.

In yet a further embodiment each of or part of the bottom electrode layers of the ultrasound transducers elements are connected to at least one semiconductor chip. The semiconductor chip can for example be an ASIC or the like. The semiconductor chip can be used to control the transmission and/or reception of the ultrasound transducer elements, for example using beamforming in order to steer the ultrasound waves at an angle with respect to the general transmission direction. In particular, external electrical connection, in particular, to ground, can be provided via the semiconductor chip.

In a further embodiment the bottom electrode layer of the ultrasound transducer element having the specific piezoelectric layer is connected to a flexible circuit for external electrical connection. In this way external electrical connection can be provided, in particular to ground. Thus, an electrical path for the ground return current can be provided. In a variant of this embodiment, the bottom electrode layer of the specific ultrasound transducer element is connected to the semiconductor chip, which is connected to the flexible circuit. Thus, the electrical path for the ground return current can be provided.

In a further embodiment, the conductive layer is applied by metallization. In this way an easy way of manufacturing, in particular coating of the conductive layer, is provided. In an example, the conductive layer can be made of gold or any other suitable conductive material that can be applied by metallization.

In a variant of this embodiment the metallization is performed by sputtering or applying conductive epoxy. Sputtering or applying conductive epoxy are particularly suitable manufacturing methods.

In another embodiment the bottom electrode layers, the top electrode layers, and the conductive layer are applied in one common metallization step to a common layer of piezoelectric material. In a variant of this embodiment the ultrasound transducer elements are cut out or diced out of the common layer of piezoelectric material after the common metallization step has been performed. By providing a common layer of piezoelectric material on which a common top electrode layer and a common bottom electrode layer and the conductive layer on the side surface is applied, the manufacturing process is simplified. The ultrasound transducer elements then only need to be cut out or diced out of the common metalized layer of piezoelectric material. In this way, also less variability in the electrical connection is provided, as there is a common top electrode layer and a common bottom electrode layer.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
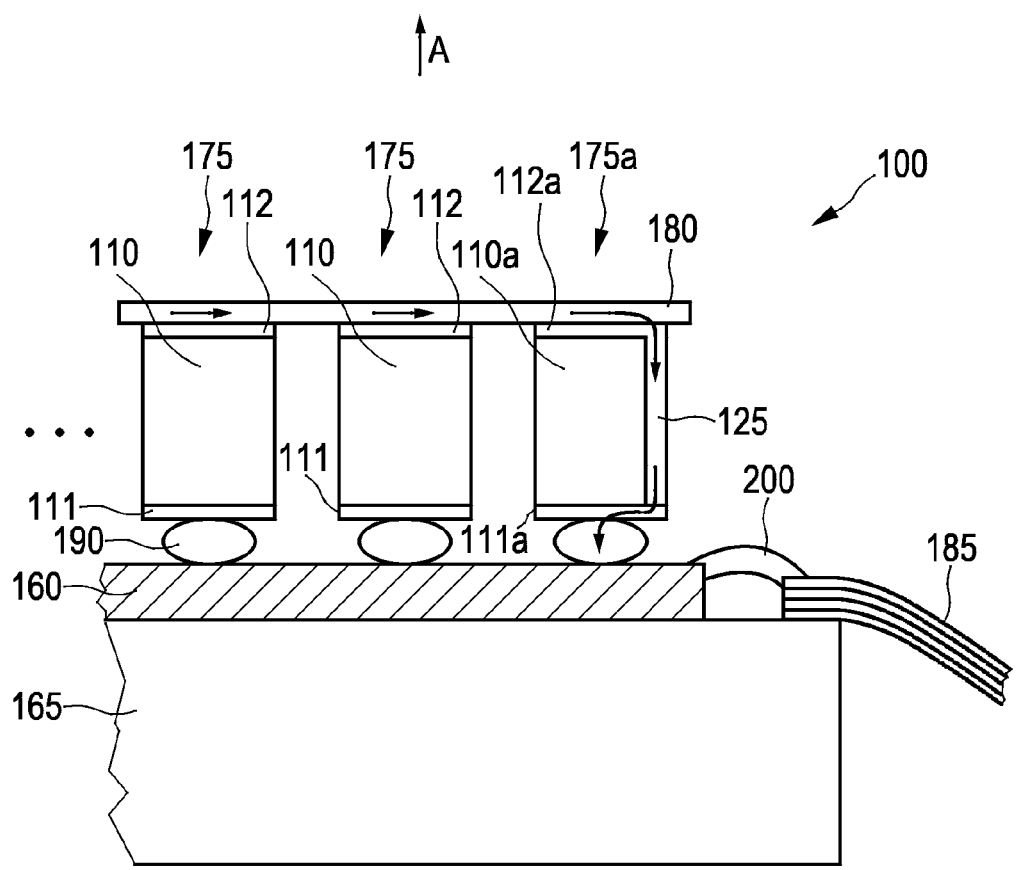
FIG. 1 shows a cross sectional view of an ultrasound transducer assembly according to an embodiment.

FIG. 1 shows a cross sectional view of an ultrasound transducer assembly 100 according to an embodiment. The ultrasound transducer assembly 100 comprises ultrasound transducer elements 175, 175a for transmitting ultrasound waves in a general transmission direction A. The ultrasound transducer elements 175, 175a can be arranged in a (one-dimensional) row or an (two-dimensional) array. For simplification purposes, in the cross sectional view of FIG. 1 only three of those ultrasound transducer elements are illustrated. It will be understood that there can be any number of additional ultrasound transducer elements arranged in the row or the array.

In the embodiment of FIG. 1, each of the ultrasound transducer elements 175, 175a comprises a piezoelectric layer 110, 110a having a top surface, a bottom surface and a side surface with respect to the general transmission direction A. The top surface and the bottom surface of the piezoelectric layer 110, 110a are each arranged perpendicular to the general transmission direction A. The side surface is arranged parallel to the general transmission direction A. Each of the ultrasound transducer elements 175, 175a further comprises a bottom electrode layer 111, 111a arranged on the bottom surface of the piezoelectric layer 110, 110a and a top electrode layer 112, 112a arranged on the top surface of the piezoelectric layer 110, 110a. With general transmission direction a general direction is meant in which the ultrasound waves are transmitted from the ultrasound transducer elements 175, 175a. As can be seen in FIG. 1, the top surface or top electrode layer 112, 112a of the piezoelectric layer 110, 110a is arranged further in front in the general transmission direction A than the corresponding bottom surface or bottom electrode layer 111, 111a of the piezoelectric layer 110. The general transmission direction A is here perpendicular to a surface formed by the tops of the ultrasound transducer elements 175, 175a. When a voltage is applied between the top electrode layer 112 and the bottom electrode layer 111 of a transducer element 175, ultrasound waves are transmitted from the piezoelectric layer 110 of that ultrasound transducer element 175 in the general transmission direction A.

A conductive layer 125 is (directly) applied at least partly on the side surface of at least one specific piezoelectric layer 110a of the piezoelectric layers, in particular on the entire side surface. The ultrasound transducer element having that specific piezoelectric layer 110a is the transducer element 175a in the embodiment of FIG. 1. As can be seen in FIG. 1, there are no intermediate layers between the piezoelectric layer 110a and the applied conductive layer 125, thus the conductive layer 125 is (directly) applied. The conductive layer 125 is applied, such that the conductive layer 125 is connected to the top electrode layer 112a and the bottom electrode layer 111a of said specific piezoelectric layer 110a of the specific transducer element 175a. In this way, a short electrical path between the top electrode 112a and an external electrical connection (via the bottom electrode 111a), in particular to ground, can be provided. Such electrical path is schematically indicated by arrows in FIG. 1. By providing this electrical path from the top electrode layer 112a to the bottom electrode layer 111a of that specific piezoelectric layer 110a of the specific ultrasound transducer element 175a, a short electrical path, in particular for ground return current, is provided and at the same time the manufacturing process is easy.

In this way, the specific ultrasound transducer element 175a having the specific piezoelectric layer 110a is created to be a dummy element not operable to transmit or receive ultrasound waves. Thus, the specific transducer element 175a is sacrificed, as is it not functioning as an ultrasound transducer element any more. However, even though this specific ultrasound transducer element 175 is sacrificed, the manufacturing of the ultrasound transducer assembly 100, which will be explained in more detail further on, is significantly simplified.

As can be seen in the embodiment of FIG. 1, the specific ultrasound transducer element 175a having the specific piezoelectric layer 110a (dummy element) is the outermost ultrasound transducer element 175a in the row or array of ultrasound transducer elements. In particular, the side surface to which the conductive layer 125 is applied is the side surface facing outward in the row or the array.

In the embodiment of FIG. 1 the ultrasound transducer assembly 100 further comprises a conductive connection layer 180 which electrically connects the top electrode layers 112, 112a. In this embodiment, the conductive connection layer 180 is (directly) applied to the top electrode layers 112, 112a. Alternatively, it can also form the top electrode layers 112, 112a. The conductive connection layer 180 connects the top electrode layers 112, 112a in order to provide a return current path, indicated by the arrows in FIG. 1, as previously explained.

As can be seen in the embodiment of FIG. 1, each of the bottom electrode layers 111, 111a of the ultrasound transducer elements 175, 175a are connected to a semiconductor chip 160. This electrical connection is provided using electrically conductive stud bumps 190. However, the electrical connection can also be provided in any other suitable way. The semiconductor chip 160 can for example be an ASIC or the like. The semiconductor chip 160 can be used to control the transmission and/or reception of the ultrasound transducer elements 175, 175a, for example using beamforming in order to steer the ultrasound waves at an angle with respect to the general transmission direction A. The semiconductor chip 160 is arranged on a backing 165 in the embodiment of FIG. 1. The backing 165 provides support for the transducer assembly. External electrical connection (to ground) is provided via the semiconductor chip (e.g. ASIC).

The semiconductor chip 160 is connected to a flexible circuit 185 using a connector 200. In this way, also the bottom electrode layer 111a of the specific ultrasound transducer element 175a having the specific piezoelectric layer 110a is connected to the flexible circuit 185 for external electrical connection. Thus, the ground return current path can be provided. More particularly, the bottom electrode layer 111a of the specific ultrasound transducer element 175a is connected to the semiconductor chip 160, which in turn is connected to the flexible circuit 185, thus providing the ground return current path.

The flexible circuit 185 can comprise a ground wire for such electrical connection. The flexible circuit 185 can further comprise system channel lines and semiconductor chip control lines (e.g. ASIC control lines). The system channel lines each transmit a data signal between a respective one of the transducer elements 175 and an external ultrasound computation system (not shown) (e.g. an ultrasound imaging system). Each data signal can for example control the transmission and/or reception of the respective transducer element 175. The semiconductor chip control lines (e.g. ASIC control lines) control functionality of the semiconductor chip (e.g. ASIC). A coaxial cable (not shown) can for example be joined to the flexible circuit 185 for external electrical connection, in particular to the ultrasound computation system. A ground or voltage and/or current source, for ground connection or connection to voltage potential, can be located in the ultrasound computation system. Alternatively, the ground or voltage and/or current source can also be located at any other suitable position, for example attached to or arranged next to the ultrasound transducer assembly.

FIGS. 2a to 2e show subsequent manufacturing steps of a method of manufacturing an ultrasound transducer assembly according to an embodiment, in particular for manufacturing the ultrasound transducer assembly 100 of the embodiment of FIG. 1. In a first step, shown in FIG. 2a, the method comprises providing a common layer 110' of piezoelectric material having a top surface, a bottom surface and a side surface. Using this common piezoelectric layer 100', for each of the ultrasound transducer elements 175, 175a a piezoelectric layer 110, 110a having a top surface, a bottom surface and a side surface with respect to the general transmission direction A can be provided.

Figure 2A:
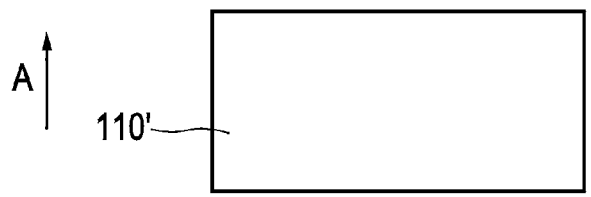
FIGS. 2a to 2e show subsequent manufacturing steps of a method of manufacturing according to an embodiment.
Figure 2B:
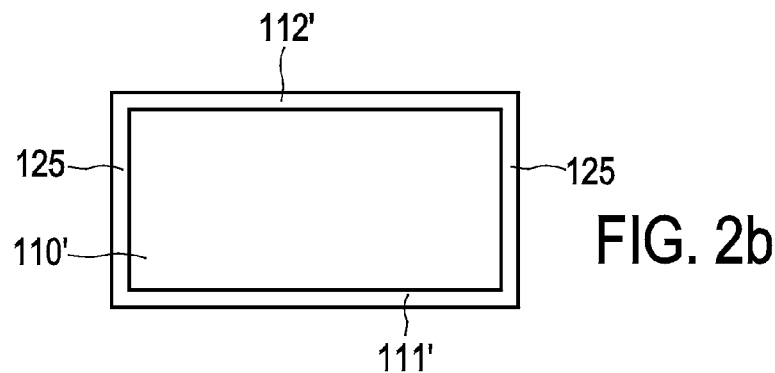

In a subsequent step, as shown in FIG. 2b, a common bottom electrode layer 111' is applied on the bottom surface of the common piezoelectric layer 100', a common top electrode layer 112' is applied on the top surface of the common piezoelectric layer 110', and the conductive layer 125 is applied on each of the side surfaces of the common piezoelectric layer 100', such that the conductive layer 125 is connected to the common top electrode layer 112' and the common bottom electrode layer 111'. The conductive layer 125 and/or the electrode layers can be applied by metallization, such for example by sputtering or applying conductive epoxy. As can be seen in FIG. 2b, the bottom electrode layers 111, 111a, the top electrode layers 112, 112a, and the conductive layer 125 are applied in one common metallization step to the common layer 110' of piezoelectric material.

Figure 2C:
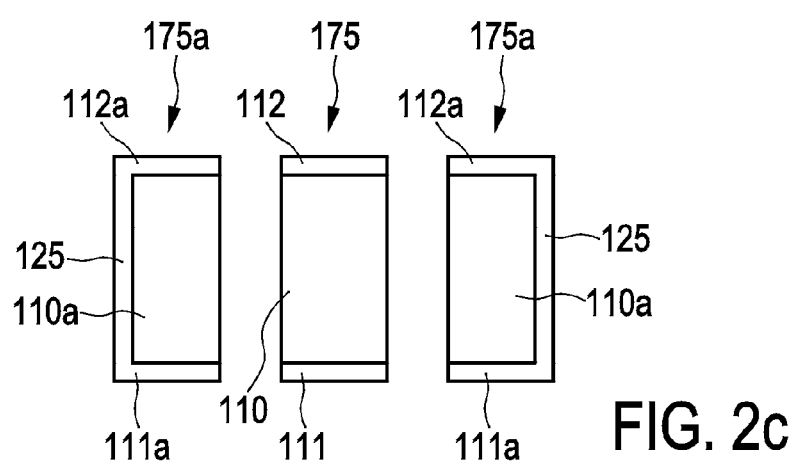

In a subsequent step, as shown in FIG. 2c, the ultrasound transducer elements 175, 175a are cut out or diced out of the coated or metalized common layer 110' of piezoelectric material after the common metallization step (as explained with reference to FIG. 2b) has been performed.

In this way it can be achieved that for each of the ultrasound transducer elements 175, 175a, a bottom electrode layer 111, 111a is arranged on the bottom surface of the piezoelectric layer 110, 110a, and a top electrode layer 112, 112a is arranged on the top surface of the piezoelectric layer 110, 110a. Further, a conductive layer 125 is (directly) applied on the side surface(s) of the specific piezoelectric layer(s) 110a, such that the conductive layer 125 is connected to the top electrode layer 112a and the bottom electrode layer 111a of that specific piezoelectric layer(s) 110a.

In FIG. 2c the specific ultrasound transducer elements 175a having the specific piezoelectric layers 110a are the two outermost ultrasound transducer elements at the two ends of the (one dimensional) row of ultrasound transducer elements. Similarly, if the ultrasound transducer elements are arranged in an (two-dimensional) array, these are the ultrasound transducer elements at the edges of the array.

Figure 2D:
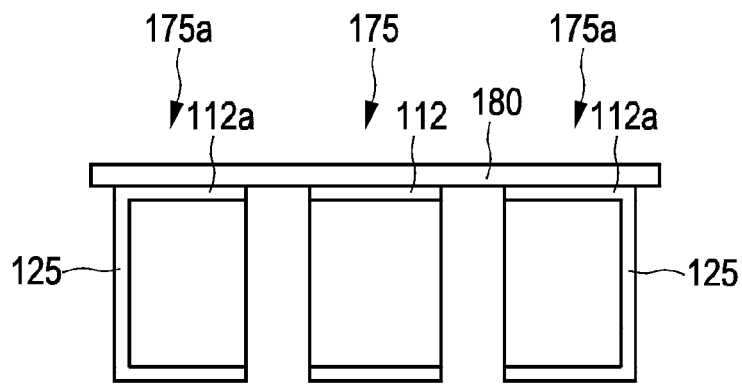

In a further step, with reference to FIG. 2d, a conductive connection layer 180 which electrically connects the top electrode layers 112, 112a can be provided. In this example, the conductive connection layer 180 is (directly) applied on the top electrode layers 112, 112a.

Figure 2E:
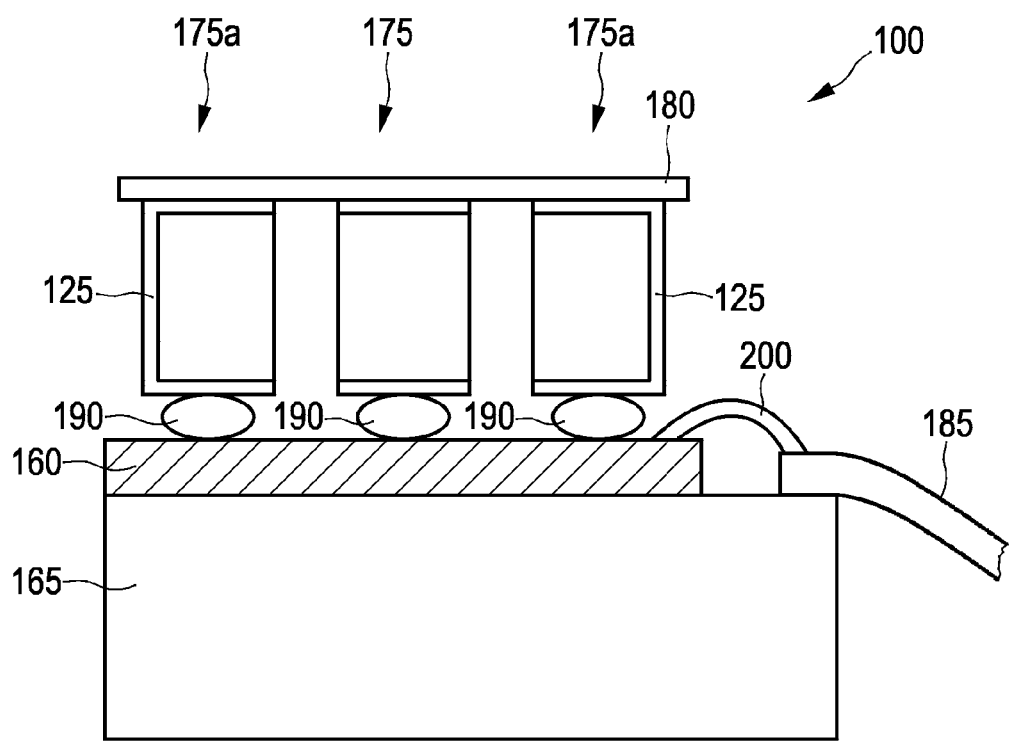

A final step for providing the ultrasound transducer assembly 100 is shown in FIG. 2e. The connected transducer elements 175, 175a can be connected to at least one semiconductor chip 160, which is for example arranged on a backing 165. As can be seen in FIG. 2e, this can for example be done by using conductive stud bumps 190. Finally, the semiconductor chip 160 can then be connected to a flexible circuit 185 using a connector 200. It will be understood that the step of FIG. 2e could also be performed before the step of FIG. 2d.

Figure 3A:
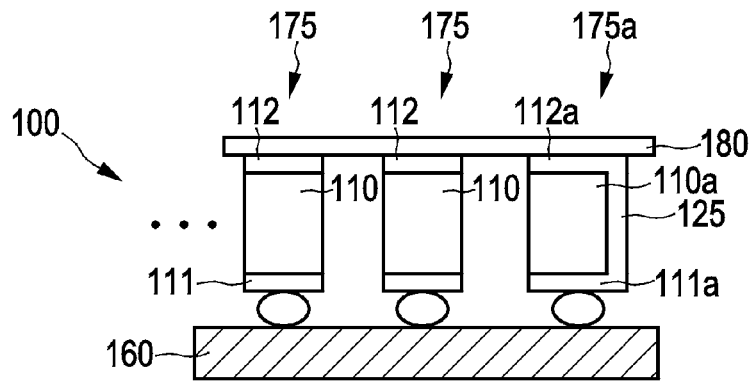
FIGS. 3a to 3g each show a cross sectional view of an ultrasound transducer assembly according to different embodiments.
Figure 3B:
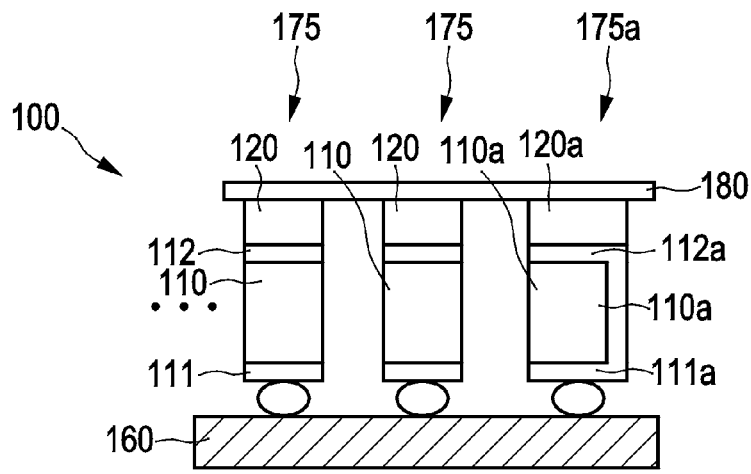

FIGS. 3a to 3g each show a cross sectional view of an ultrasound transducer assembly 100 according to different embodiments. FIG. 3a shows the basic embodiment as explained with reference to FIG. 1 or FIGS. 2a to 2e. FIG. 3b shows an embodiment which differs from the basic embodiment of FIG. 3a by an additional first matching layer 120 applied to the top electrode 112, 112a of each ultrasound transducer element 175, 175a. The embodiment of FIG. 3c differs from the basic embodiment of FIG. 3a by a first matching layer 120 applied to the top electrode 112, 112a of each transducer element 175, 175a and a second matching layer 130 applied to the first matching layer 120 of each transducer element 175, 175a. By providing the matching layer(s) 120, 130, impedance matching to the body of the user (patient), on which the ultrasound transducer assembly 100 can be placed, is achieved.

The matching layer(s) 120, 130 can in particular be made of a conductive material (e.g. graphite). In this way, electrical connection from the top electrode 112 to the conductive connection layer 180, as previously described, can be provided.

Figure 3C:
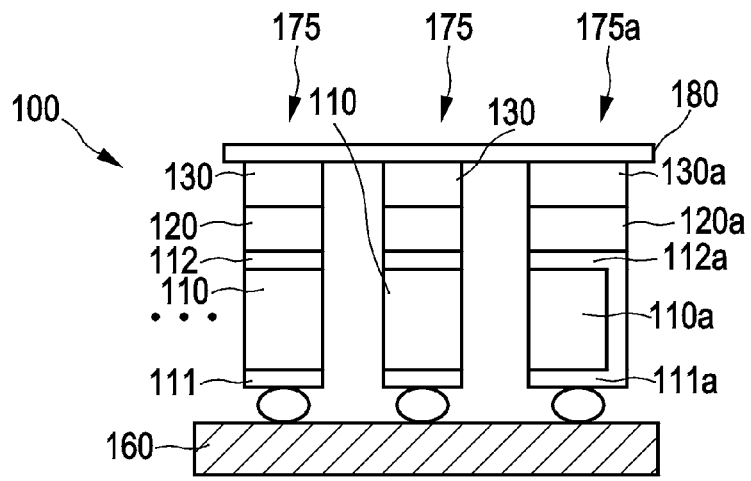
Figure 3D:
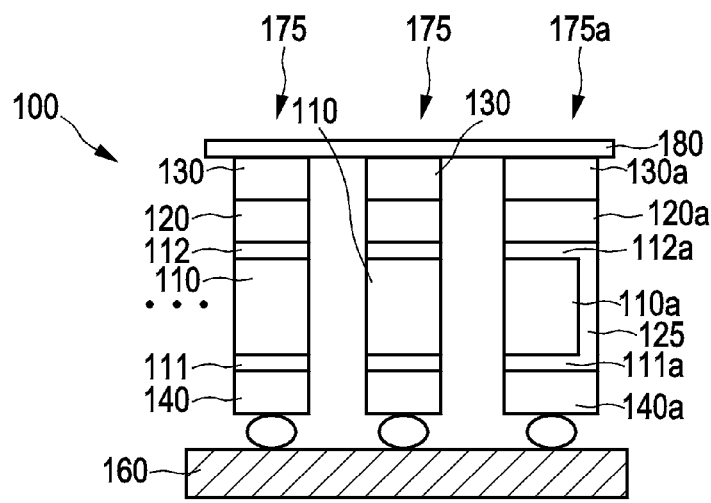

The embodiment of FIG. 3d differs from the embodiment of FIG. 3c by an additional de-matching layer applied to the bottom electrode layer 111, 111a of each transducer element 175, 175a. By providing the de-matching layer 140 to the bottom electrode, reflection of basically all of the transmitted energy of the ultrasound waves in the general transmission direction A can be achieved. The de-matching layer 140 can in particular be made of a conductive material (e.g. a metal, such as Tungsten, or a carbide, such as Tungsten carbide).

Figure 3E:
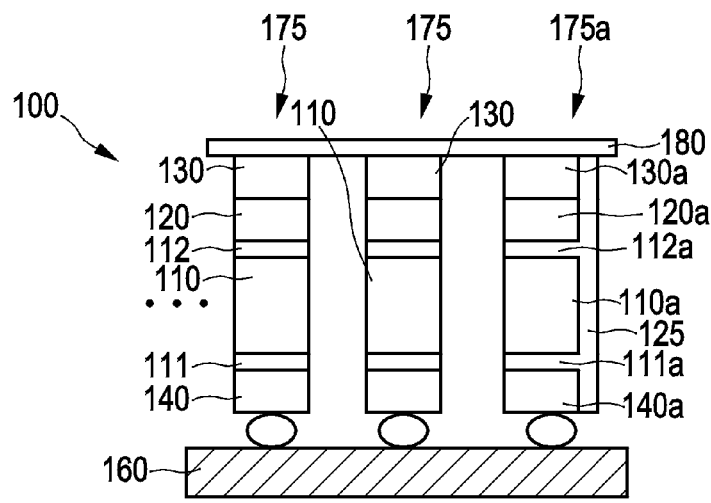

The embodiment of FIG. 3e differs from the embodiment of FIG. 3d in that the conductive layer 125 is further (directly) applied on the side surface of the first matching layer 120a, the second matching layer 130a and the de-matching layer 140a for the specific transducer element 175a. Applying the conductive layer 125 on the whole side surface of the specific ultrasound transducer element 175a (stack of layers) is easier than applying it on only part of the side surface. Thus, the whole side surface of the stack of layers is coated with the conductive layer 125 in the embodiment of FIG. 3e.

Figure 3F:
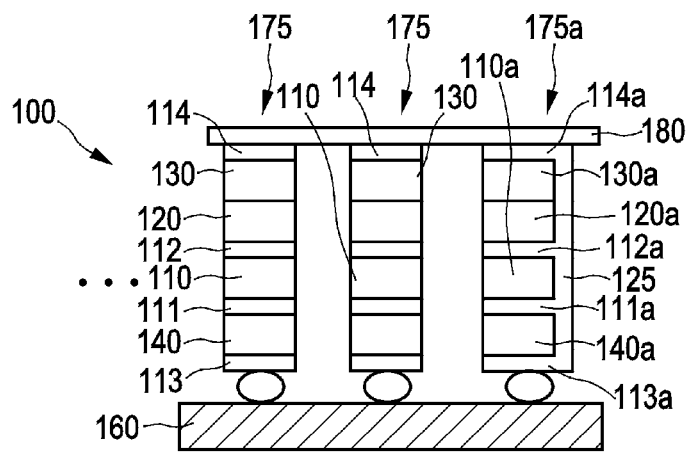

The embodiment of FIG. 3f differs from the embodiment of FIG. 3e, for each transducer element, by an additional top conductive layer 114, 114a applied to the upmost matching layer 130, 130a and an additional bottom conductive layer 113, 113a applied to the bottom most de-matching layer 140, 140a. Thus, the top conductive layer 114, 114a and the bottom conductive layer 113, 113a are applied on the top surface and the bottom surface of the stack of layers. Thus, the stack of layers can be coated on all sides, providing an easier way of manufacturing.

Figure 3G:
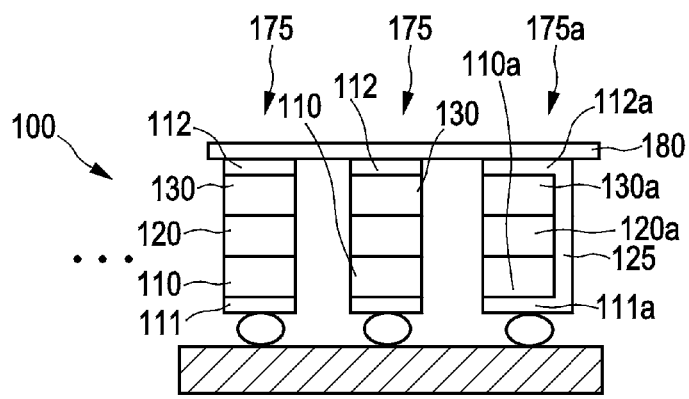

In the embodiment of FIG. 3g the top electrode is not (directly) applied to the top surface of the piezoelectric layer, but there are intermediate layers between the piezoelectric layer and the top electrode layer. Each of the ultrasound transducer elements 175, 175a comprises a piezoelectric layer 110, 110a having the top surface, the bottom surface and the side surface. Each of the ultrasound transducer elements 175, 175a comprises a bottom electrode layer 111, 111a arranged on the bottom surface of the piezoelectric layer 110, 110a. A first matching layer 120, 120a is applied on the top surface of each transducer element 175, 175a, and a second matching layer 130 is applied on the first matching layer 120. The top electrode layer 112, 112a is then applied on the second matching layer 130. Thus, in this embodiment of FIG. 3g, contrary to the embodiments of the previous figures, the top electrode layer 112, 112a is not (directly) applied on the top surface of the piezoelectric layer 110, 110a, but there are intermediate layers in between. However, as the matching layers 120, 130 are conductive, the top electrode layer 112, 112a can still act as a top electrode for the piezoelectric element 110, 110a. It will be understood that any number (e.g. one) of intermediate layers (e.g. matching layer(s)) can be arranged in between. In the same way (not shown in FIG. 3g), the bottom electrode layer could not be (directly) applied to the bottom surface of the piezoelectric layer, as shown in FIG. 3g, but could be applied on the bottom surface of a de-matching layer 140 which is applied on the bottom surface of the piezoelectric layer.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An ultrasound transducer assembly comprising at least one row of ultrasound transducer elements for transmitting ultrasound waves in a general transmission direction comprising:
   a semiconductor chip; and
   the ultrasound transducer elements of the row each comprising:
   a piezoelectric layer having a top surface, a bottom surface and a side surface with respect to the general transmission direction;
   a bottom electrode layer located on the bottom surface which is electrically coupled to the semiconductor chip; and
   a top electrode layer located on the top surface and facing the general transmission direction;
   a conductive connection layer electrically coupling the top electrode layers of the elements of the row,
   wherein a conductive layer is applied on the side surface of the piezoelectric layer of at least one of the elements of the row, such that the conductive layer electrically couples the top electrode layer and the bottom electrode layer of the element,
   wherein the bottom electrode layer of the at least one of the elements electrically couples the conductive connection layer to the semiconductor chip.

2. The ultrasound transducer assembly of claim 1, wherein the ultrasound transducer element having the side surface conductive layer is a dummy element not operable to transmit or receive ultrasound waves.

3. The ultrasound transducer assembly of claim 1, wherein the ultrasound transducer element having the side surface conductive layer is the outermost ultrasound transducer element in the row of the ultrasound transducer elements.

4. The ultrasound transducer assembly of claim 3, wherein the side surface to which the conductive layer is applied is the side surface facing outward in the row of the ultrasound transducer elements.

5. The ultrasound transducer assembly of claim 1, further comprising at least one de-matching layer applied to the bottom electrode layer.

6. The ultrasound transducer assembly of claim 5, wherein the conductive layer is further applied on the side surface of the de-matching layer.

7. The ultrasound transducer assembly of claim 1, wherein each of the bottom electrode layers of the ultrasound transducers elements is connected to the semiconductor chip.

8. The ultrasound transducer assembly of claim 1, wherein the bottom electrode layer of the ultrasound transducer element having the side surface conductive layer is connected to a flexible circuit for external electrical connection.

9. A method of manufacturing an ultrasound transducer assembly comprising ultrasound transducer elements for transmitting ultrasound waves in a general transmission direction, the method comprising, for each of the ultrasound transducer elements of a row of transducer elements:
   providing a piezoelectric layer having a top surface, a bottom surface and a side surface with respect to the general transmission direction;
   applying a bottom electrode layer to the bottom surface; and
   applying a top electrode layer to the top surface facing the general transmission direction;
   applying a conductive connection layer which electrically couples the top electrode layers of the elements of the row;
   applying a conductive layer on the side surface of at least one of the transducer elements, such that the conductive layer is connected to the top electrode layer and the bottom electrode layer of the one of the transducer elements,
   electrically coupling the bottom electrode layers of the elements of the row to a semiconductor chip, wherein the transducer element with the side surface conductive element electrically couples the conductive connection layer to a return current path of the semiconductor chip.

10. The method of claim 9, wherein the conductive layer is applied by metallization.

11. The method of claim 10, wherein the metallization is performed by sputtering or applying conductive epoxy.

12. The method of claim 9, wherein bottom electrode layers, the top electrode layers, and the conductive layer are applied in one common metallization step to a common layer of piezoelectric material.

13. The method of claim 12, wherein the ultrasound transducer elements are cut out or diced out of the common layer of piezoelectric material after the common metallization step has been performed.

* * * * *